(12) United States Patent
Donitzky et al.

(10) Patent No.: US 6,802,837 B2
(45) Date of Patent: Oct. 12, 2004

(54) DEVICE USED FOR THE PHOTOREFRACTIVE KERATECTOMY OF THE EYE USING A CENTERING METHOD

(75) Inventors: Christof Donitzky, Eckental (DE); Joachim Löffler, Heroldsberg (DE)

(73) Assignee: Wavelight Laser Technologie AG, Erlangen (DE)

( * ) Notice: Subject to any disclaimer, the term of this patent is extended or adjusted under 35 U.S.C. 154(b) by 0 days.

(21) Appl. No.: 09/913,564

(22) PCT Filed: Dec. 22, 2000

(86) PCT No.: PCT/EP00/13173

§ 371 (c)(1),
(2), (4) Date: Aug. 15, 2001

(87) PCT Pub. No.: WO01/45606

PCT Pub. Date: Jun. 28, 2001

(65) Prior Publication Data

US 2002/0128634 A1 Sep. 12, 2002

(30) Foreign Application Priority Data

Dec. 22, 1999 (DE) .......................................... 199 62 107

(51) Int. Cl.[7] .............................................. A61B 18/18
(52) U.S. Cl. .............................. 606/5; 606/10; 606/12; 606/17; 351/208; 351/210; 351/211
(58) Field of Search ............................. 606/4–6, 10, 11, 606/13, 16–19; 351/208–211

(56) References Cited

U.S. PATENT DOCUMENTS

| 4,848,340 A | * | 7/1989 | Bille et al. ................ 128/303.1 |
| 4,881,808 A | * | 11/1989 | Bille et al. ................... 351/221 |
| 5,098,426 A | * | 3/1992 | Sklar et al. ..................... 606/5 |
| 5,604,818 A | | 2/1997 | Saitou et al. |
| 5,644,642 A | | 7/1997 | Kirschbaum |
| 5,997,141 A | * | 12/1999 | Heacock ..................... 351/221 |
| 6,019,754 A | * | 2/2000 | Kawesch ....................... 606/4 |
| 6,030,376 A | * | 2/2000 | Arashima et al. ............... 606/4 |
| 6,299,307 B1 | * | 10/2001 | Oltean et al. ............... 351/210 |
| 6,406,473 B1 | * | 6/2002 | Shimmick et al. ............. 606/5 |
| 6,585,375 B2 | * | 7/2003 | Donitzky et al. ........... 351/219 |

FOREIGN PATENT DOCUMENTS

| DE | 197 02 335 | 8/1998 |
| EP | 0 770 370 | 5/1997 |
| WO | WO 95/27453 | 10/1995 |
| WO | WO 95/28879 | 11/1995 |
| WO | WO 95/28989 | 11/1995 |

OTHER PUBLICATIONS

H. Uozato and G.L. Guyton, American Journal of Ophtalmology 103: 261–275, Mar. 1987.

* cited by examiner

*Primary Examiner*—Linda C. M. Dvorak
*Assistant Examiner*—Ahmed Farah
(74) *Attorney, Agent, or Firm*—Woodard, Emhardt, Moriarty, McNett & Henry LLP

(57) ABSTRACT

The invention relates to a device used for the photorefractive keratectomy of the eye, especially LASIK, uses an UV laser beam for ablating parts of the cornea. A centering light beam is arranged coaxially with respect to the fixing light beam and has a wavelength different from that of the fixing light beam. The device is provided with devices for measuring and evaluating the position of the scattered light/Fresnel reflection of the centering light beam on the front face of the cornea. The point in which the centering light beam passes through the front face of the cornea is used as the center of ablation.

5 Claims, 1 Drawing Sheet

DEVICE USED FOR THE PHOTOREFRACTIVE KERATECTOMY OF THE EYE USING A CENTERING METHOD

The present invention relates to a device used for the photorefractive keratectomy of the eye, comprising an UV laser beam (UV) for ablating parts of the cornea, and a fixation light beam which has a wavelength in the visible region and which is directed onto the eye.

In photorefractive keratectomy (PRK) a defective vision of the human eye is corrected in that part of the cornea is re-shaped. A special PRK method, which is substantially gaining significance at present, is LASIK. According to the LASIK method, a flap is cut into the cornea and opened up. Subsequently, an UV laser beam (normally an Excimer laser beam having a wavelength of 193 nm) is directed onto the exposed parts of the cornea (parts of the cornea uncovered by the flap) so as to ablate material there. After the desired ablation, the flap is clapped down and heals with the cornea.

The present invention relates to PRK in general and to the LASIK method in particular.

In the case of PRK and LASIK, respectively, the ablation profile, i.e. the local distribution of the thickness of the corneal regions to be ablated, depends on the nature of the visual defect to be corrected. When the visual defect to be corrected is myopia or hyperopia, the ablation profile is rotationally symmetric; when astigmatism is to be corrected, the ablation profile is asymmetric. The latter also applies to the correction of higher-order visual defects (wavefront correction, aberration correction).

For all the above-mentioned corrections it is, however, normally necessary to define an axis with regard to which the ablation is centered. The ablation according to the ablation profile is carried out according to algorithms known to those skilled in the art, i.e. the UV radiation is directed onto the cornea to be modified, in a temporal and local distribution corresponding to the algorithm. The algorithm needs an axis which defines the centre of the ablation profile, i.e. the axis extends through the cornea surface to be treated and the ablation profile is represented with regard to the point of intersection between this axis and the cornea surface. This permits centering of the PRK and LASIK methods, and this is what matters in the present invention.

The centering of corneal surgical procedures is made more difficult by the circumstance that the human eye is not a centered optical system, i.e. a common optical axis of the cornea, anterior chamber, lens, vitreous body chamber and fovea of the eye does not exist. H. UOZATO and G. L. GUYTON describe quite generally the problem of centering in the case of corneal surgical procedures, cf. the American Journal of Ophthalmology 103:261–275, March 1987. This prior art is assumed to be known in the following. In this prior art it is suggested that the centre of the entrance pupil of the eye, but not the so-called "visual axis", should be used for centering corneal surgical procedures and it is explained how this can be done. A so-called optical "line of sight" is defined, which connects the fixation point to the centre of the entrance pupil. As has already been mentioned, the above-defined line of sight is to be understood optically but not geometrically. The fixation point corresponds to the above-mentioned fixation light beam, i.e. it is the point fixated by the patient. H. UOZATO et al. (see above) suggest that the point of intersection between said line of sight and the front face of the cornea should be used as a centre for the corneal surgical procedure. This prior art is taken as a basis in the present invention, i.e. the point where the line of sight passes through the front face of the cornea is chosen as the centre of refractive correction. In the LASIK method the term "front face of the cornea" is to be interpreted such that the exposed surface of the cornea (which can be located e.g. in the stroma) defines the above-mentioned piercing point (point of passage).

Theoretically, the following course of action could be taken for determining said piercing point: the line of sight connects the fixation point to the fovea. The fixation light forms a reflex (i.e. it is reflected) on the front face of the cornea, the so-called scattered light/Fresnel reflex. Hence, this scattered light/Fresnel reflex starts from the piercing point and permits therefore a determination of the position of said piercing point. The scattered light/Fresnel reflex should not be confused with the Purkinje-Sanson image (cf. the prior art cited at the beginning). It follows that, making use of this method, the scattered light/Fresnel reflex of the fixation light beam could be chosen as a means of marking the ablation centre. The image of the scattered light/Fresnel reflex has, however, an extremely weak luminous intensity and is, in addition, swamped out by the Purkinje-Sanson image so that measurements according to this method would be extremely difficult.

WO 95/27453 describes the use of an infrared light beam which is directed onto the cornea coaxially with the actual ablation beam (Excimer laser beam). Prior to each ablation pulse, the position of the corneal front face reflex of this IR beam is determined by means of a so-called eye tracking camera. Through image evaluation, a comparison is carried out between a desired position and an actual position of this reflex relative to a reference point of the eye tracking. If the actual position determined deviates from the desired position, an attempt will be made to equalize this difference by means of a control element (the scanner). If this cannot be done, the ablation pulse will not be released. In this prior art, a localization of the point at which the fixation light beam passes through the front face of the cornea does not take place. It follows that, in the case of this prior art, it is also impossible to choose this point as a centre for the subsequent refractive correction of the cornea.

WO 95/28879 and WO 95/28989 describe methods for determining the eye position by means of four IR diodes which are reflected with different intensities on an optical interface on or in the eye. The position of the eye is calculated on the basis of the measured reflected intensities of the radiation.

It is the object of the present invention to provide a device and a method by means of which centering for photorefractive keratectomy, especially LASIK, can be carried out in a reliable manner.

According to the present invention, this is achieved by means of a device of the type specified at the beginning, which comprises, in addition to the UV laser beam used for ablating the cornea and the fixation light beam which must be in the region visible to the patient, a centering light beam extending coaxially with the fixation light beam and having a wavelength different from that of the fixation light beam, means being provided for measuring the scattered light/Fresnel reflex of said centering light beam on the front face of the cornea.

In the LASIK method, the "front face of the cornea" is the cornea surface that is exposed when the flap has been opened up.

Due to the fact that the wavelength chosen for the centering light beam is different from that of the fixation light beam, it is possible to separate the two beams from one another when the reflex is being measured and to discriminate them so that the fixation light will no longer disturb the measurement.

The centering light beam has preferably a wavelength in the infrared region, especially in the range from 800 to 1,100 nm.

A specially preferred embodiment of the invention is so conceived that a camera is used for measuring the position of the scattered light/Fresnel reflex of the centering light. In devices used for the photorefractive keratectomy of the eye, such a camera is often already provided for other reasons, in particular for so-called eye tracking. The eye tracking technique is described e.g. in DE 197 02 335 C1; also this prior art is assumed to be known in the following. According to this prior art "eye tracking" is carried out as follows: when performing photorefractive keratectomy, and in particular LASIK, it is important that the relative position of the ablating laser beam and the eye is precisely known. In the case of optical fixation, which is preferably used also in the present invention, the patient is requested to look precisely at the point defined by the fixation light beam so that the eye will maintain the same position during the whole surgical operation. However, the patient does not normally succeed in doing so, at least not with sufficient reliability so that movements of the eye occur which may seriously impair the whole ablation process. "Eye tracking" means that the movements of the eye are determined so that the laser beam used for the ablation can then be controlled (caused to follow) in accordance with the eye movements. The above-cited prior art describes how during "eye tracking" images of the eye are recorded by means of a camera (solid state camera, CCD) and processed in rapid succession. A change in the position of the eye can be determined from successive images, and the ablation laser beam is then caused to follow in accordance with the eye movement with the aid of suitable beam control means (e.g. a galvanometric scanner). The cited prior art also teaches that, for determining a movement of the cornea, the centre of the pupil should be determined and the movement thereof should be ascertained. In the case of this photographic evaluation, the eye is normally illuminated with IR radiation and the image of the eye, in particular of the iris with the pupil, is recorded with the camera for the purpose of evaluation. This IR radiation, by means of which the eye is illuminated for the above-mentioned purpose, can be used together with the present invention and will neither be specially mentioned nor described in the following. Even though the centering light beam has wavelengths in the IR region, the IR rays reflected by the eye can be deflected by means of suitable partly reflecting mirrors and separated from the reflections of other wavelengths in such a way that the position of the pupil, especially the geometrical centre thereof, as well as the position of the scattered light/Fresnel reflex can be determined by means of the camera and a computer connected thereto. Hence, it is possible to establish a correlation between the ablation centre to be located and the geometrical centre of the pupil, i.e. to form e.g. the vector from the geometrical centre of the pupil to said reflex and to define subsequently, on the basis of this vector, the ablation centre for the execution of the ablation algorithm during the ablation. The measuring accuracy with regard to the vector can then be improved e.g. by forming an average value over a plurality of individual measurements. It is also possible to determine the vector for different pupil diameters and to carry out averaging over these subsequently.

In the following, an embodiment of the invention will be explained in detail making reference to the drawing, in which.

Figure 1:
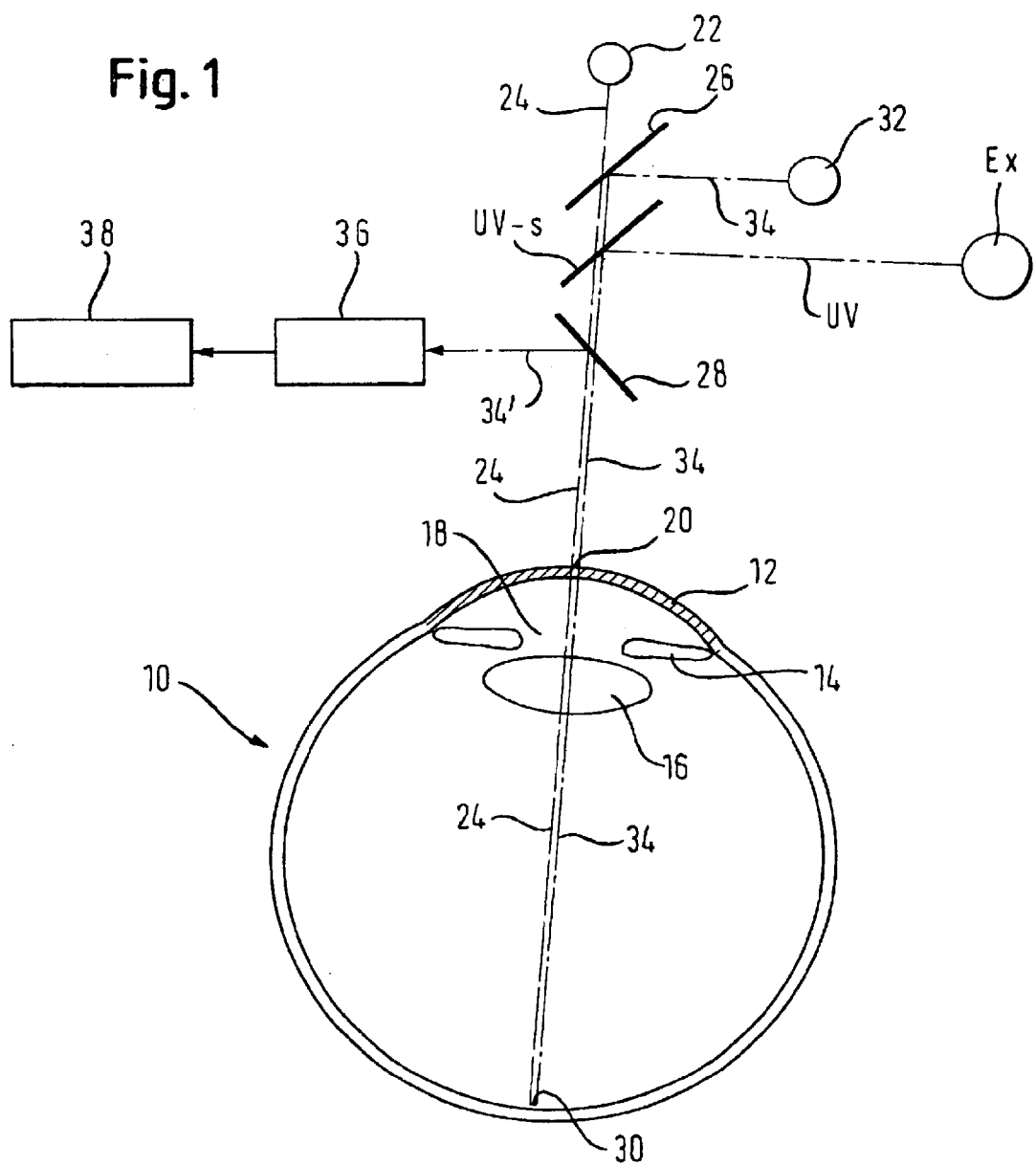
FIG. 1 shows schematically a device used for the photorefractive keratectomy of the eye.

The eye 10 schematically shown in FIG. 1 has a cornea 12, an iris 14, a lens 16 and a lens 16 and a pupil 18.

A fixation light source 22, which is known per se, emits a fixation light beam 24 which pierces the front face of the cornea 12 at point 20. The wavelength of the fixation light beam 24 is such as to be visible to the patient, i.e. it lies e.g. in the green region of the spectrum. The light source used as a fixation light source 22 is normally a diode. The fixation light beam 24 is stationary and the patient is requested to fixate the fixation light source which seems punctiform to him.

An Excimer laser Ex emits the actual ablation beam, i.e. the beam by means of which the cornea 12 is re-shaped. This ablation beam UV (e.g. 193 nm) is deflected via a mirror UV-S and scanned over the cornea 12 according to an ablation algorithm so that the desired ablation profile will ablated, i.e. the ablation beam is not stationary. The means for scanning the ablation beam are known as such and not shown in the figure in detail.

The fixation light beam 24 passes through the cornea and the pupil 18 and is imaged on the fovea. It is therefore also referred to as "line of sight". Hence, this line of sight connects the fixation point (i.e. the point of the fixation light source 22) to the centre of the entrance pupil on the object side. The "entrance pupil" is the virtual image of the real pupil seen by a viewer who looks at the eye.

The point 20 at which the fixation light beam 24 pierces the front face of the cornea 12 is chosen as a centre for the ablation, i.e. the ablation profile according to which the ablation beam UV is scanned over the cornea 12 is centered onto the point 20 at which the fixation light beam 24 pierces the exposed front face of the cornea 12. In the case of the LASIK method, the front face of the cornea is, in this sense, the exposed surface, when the so-called flap has been opened up. In order to determine the piercing point 20 on the cornea 12, a centering light source 32 is used, said centering light source 32 emitting a laser beam in the infrared region in the embodiment shown. This centering light beam 34 is directed via a partly reflecting mirror 26 onto the cornea 12 coaxially with the fixation light beam 24. In the figure, the fixation light beam 24 and the centering light beam 34 are shown in parallel juxtaposition, but, in actual fact, they extend coaxially, i.e. on a common central axis. This means that the centering light beam 34, which is stationary during the operation, will also pierce the front face of the cornea 12 at the piercing point 20. In the present embodiment, the centering light beam 34 has a wavelength in the infrared region, e.g. in the range from 800 to 1,100 nm. It is important that the centering light beam 34 has a wavelength which is different from the wavelength of the fixation light beam 24 so that reflections and images, which are produced by the two beams, can be discriminated from one another, i.e. the different wavelengths permit a measurement of a reflex of the centering light beam 34 on the front face of the cornea 12 without disturbance by the fixation light beam. The piercing point 20 is consequently measured by measuring the scattered light/Fresnel reflex of the centering light beam on the front face of the cornea. For this purpose, a partly reflecting mirror 28 is used, which directs the scattered light/Fresnel reflex 34' of the centering light beam onto a camera 36. In the embodiment shown, the camera 36 is part of the device also for other reasons, viz. as a so-called "eye tracking camera" (cf. DE 197 02 335 and the prior art cited therein).

The use of a special centering light beam 34 for the determination of the piercing point 20 of the stationary radiation on the front face of the cornea has, in comparison with the use of the fixation light beam 24 for the same purpose, the advantage that a reflex which has a comparatively high luminous intensity and which is not swamped out by other images can be evaluated by means of the camera 36 and an evaluation computer 38 following said camera. In addition, the scattered light/Fresnel reflex of the fixation light itself is swamped out by the Purkinje-Sanson image so that this reflex is difficult to evaluate.

Figure 2:
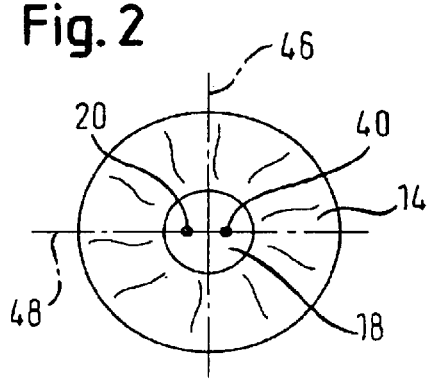
FIGS. 2 and 3 show details of specific images and reflexes of an eye occurring when a device according to FIG. 1 is used.
Figure 3:
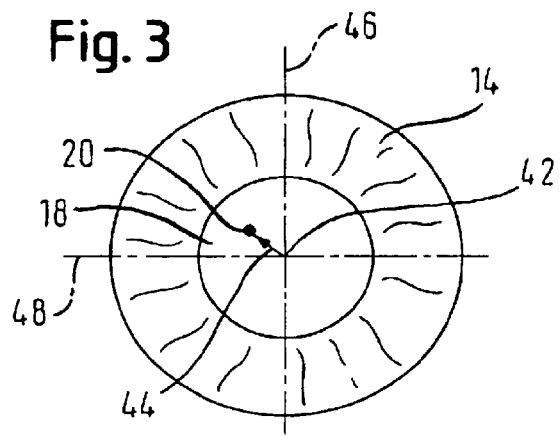

The camera 36 and the computer 38, into which the measurement values of the camera are inputted, define a so-called eye tracking system (cf. the above-cited prior art). For this purpose the eye is illuminated with independent radiation, e.g. infrared radiation (not shown), and e.g. the pupil 18 is measured by means of its boundary, so as to determine in particular the geometrical centre of the pupil (the so-called "centre of gravity of the pupil"). In addition, the system comprising the camera 36 and the computer 38 also measures the position of the scattered light/Fresnel reflex of the centering light beam 34 on the front face of the cornea 12, i.e. at the position of the piercing point 20. The camera 36 is therefore infrared sensitive in the embodiment shown. The system comprising the camera 36 and the computer 38 preferably determines the relative position between the piercing point 20 and the geometrical centre ("centre of gravity") of the pupil 18. This is explained in FIGS. 2 and 3:

FIG. 2 shows the iris 14 and the pupil 18 of the eye in a schematic top view. The virtual image 40 of the light source (here 22 and/or 32, depending on the wavelength measured) is referred to as the "first Purkinje-Sanson image" in the literature. The geometrical centre of the pupil 18 is the point of intersection of the two axes 46 and 48. FIG. 2 also shows the scattered light/Fresnel reflex of the centering light beam 34 on the front face of the cornea 12, i.e. the piercing point 20. Also FIG. 3 shows, in a slightly enlarged representation, this piercing point 20, which is measured in the manner described hereinbefore, and it shows the geometrical centre 42 of the pupil 18 as well as the vector 44 which connects the geometrical centre 42 of the pupil and the piercing point 20. In the case of (unintentional) movements of the eye, the eye tracking system comprising the camera 36 and the computer 38 determines, in a manner known per se, the respective eye position, i.e. the deviation of the eye position from the desired normal position according to FIG. 1; the ablation beam UV is caused to follow accordingly, i.e. adapted to the actual eye position, in correspondence with the ablation profile. The vector 44 predetermines the centre for the ablation and relates this centre to the geometrical centre of the pupil (="centre of gravity of the pupil") which is determined by the eye tracking system, in a manner known per se, anyhow.

In order to improve the measuring accuracy, the vector 44 can be calculated by averaging via a plurality of individual measurements. The vector can also be determined in the case of different pupil diameters so as to carry out averaging over these.

What is claimed is:

1. A device used for the photorefractive keratectomy of the eye, comprising an UV laser beam (UV) for ablating parts of the cornea, a fixation light beam (24) which has a wavelength in the visible region and which is directed onto the eye, and means for determining the point (20) at which the fixation light beam (24) passes through the front face of the cornea (12), comprising a centering light beam (34) which is directed onto the eye coaxially with the fixation light beam (24) and which has a wavelength different from that of said fixation light beam, and means (28, 36) for measuring the position (20) of the scattered light/Fresnel reflex of said centering light beam (34) directly impinging on the front face of the cornea (12).

2. A device according to claim 1, wherein the centering light beam (34) has a wavelength in the infrared region.

3. A device according to claim 2, wherein the centering light beam (34) has a wavelength in the range from 800 to 1,100 nm.

4. A device according to claim 1, wherein the means for measuring the position (20) of the scattered light/Fresnel reflex of the centering light beam (34) include a camera (36).

5. A device according to claim 4, wherein the camera (36) is connected to a computer (38) which, making use of the measurement data, determines the geometrical center (42) of the pupil and the position (20) of the scattered light/Fresnel reflex of the centering light beam (34) on the front face of the cornea.

* * * * *